United States Patent [19]

Bashyam et al.

[11] Patent Number: 5,119,678
[45] Date of Patent: Jun. 9, 1992

[54] PULSE ECHO AND THROUGH TRANSMISSION ULTRA-SOUND

[75] Inventors: Manohar Bashyam, Mason; David C. Copley, Loveland, both of Ohio

[73] Assignee: General Electric Company, Cincinnati, Ohio

[21] Appl. No.: 456,992

[22] Filed: Dec. 26, 1989

[51] Int. Cl.⁵ ............................................. G01N 29/00
[52] U.S. Cl. ........................................ 73/602; 73/614
[58] Field of Search ................. 73/599, 597, 602, 632, 73/614, 623, 644

[56] References Cited

U.S. PATENT DOCUMENTS

| | | | |
|---|---|---|---|
| 2,971,372 | 2/1961 | Lewis et al. | 73/600 |
| 4,117,732 | 10/1978 | Brazhnikox | 73/599 |
| 5,175,441 | 11/1979 | Urbanek et al. | 73/599 |
| 4,327,588 | 5/1982 | North | 73/599 |
| 4,475,398 | 10/1984 | Tjornehoj et al. | 73/599 |
| 4,594,897 | 6/1986 | Bantz | 73/600 |

FOREIGN PATENT DOCUMENTS

| | | |
|---|---|---|
| 59-204761 | 11/1984 | Japan . |
| 60-86462 | 5/1985 | Japan . |
| 1320742 | 6/1987 | U.S.S.R. . |

OTHER PUBLICATIONS

ASM Handbook Committee; *Metals Handbook;* 8th Edition; vol. 11; pp. 170–174.
Manohar Bashyam, "An Improved Display Technique For Ultrasonic Through Transmission Inspection of Composite Materials to Quantify Defects", Drexel University Symposium on Ultrasound Imaging, Sep. 21–23, 1987.

*Primary Examiner*—Hezron E. Williams
*Assistant Examiner*—Louis M. Arana
*Attorney, Agent, or Firm*—Jerome C. Squillaro; Charles L. Moore, Jr.

[57] ABSTRACT

A method for locating and identifying defects in a variable geometry workpiece using first and second transceivers positioned of a preselected distance apart adjacent opposite surfaces of the workpiece and aligned to direct ultrasonic signals toward each other through the workpiece. An ultrasound signal is transmitted from each transceiver toward the workpiece. Signal reflections from each adjacent workpiece surface are detected and used to compute workpiece thickness. Signals from one transceiver are detected at the other transceiver and their intensity determined. The signal intensity is normalized in proportion to the obtained workpiece thickness to establish a signal intensity independent of workpiece thickness. In one form, at least three signal processing paths, each having a different preselected gain, provide three signals of different amplified intensities for each measurement point. The one of the signals having the greatest amplitude not exceeding an established maximum processable signal intensity is selected and the actual intensity of the signal passing through the workpiece is computed by correlating the amplitude of the selected one of the three signals with the gain of the channel from which the signal is selected. A signal intensity corresponding to the actual intensity is displayed on an intensity responsive display for each measurement point after the actual intensity is adjusted for workpiece thickness.

6 Claims, 4 Drawing Sheets

PULSE ECHO AND THROUGH TRANSMISSION ULTRA-SOUND

The present invention relates to a method and apparatus for ultrasonic detection of flaws or discontinuities in a workpiece.

BACKGROUND OF THE INVENTION

Ultrasonic inspection techniques are used in many applications where non-destructive evaluation of a workpiece is required. One application of such ultrasonic inspection is in the inspection of composite fiber reinforced aircraft propeller blades. Such blades are typically formed from a plurality of layers of composite fibers (graphite, boron or S-glass, for example) laid over each other and adhesively bonded. Any separation of the fiber layers due to an incomplete bond or void in the blade may detrimentally affect blade strength. Ultrasonic inspection techniques can be used to identify and locate such flaws in a composite fiber reinforced blade.

One disadvantage of ultrasonic inspection is that ultrasound is attenuated by the material which is being inspected. Any variation in the geometry of a part being inspected will cause variation in the amplitude of any through transmission. Since anomalies in a part being inspected are detected by such amplitude variations, it becomes difficult to distinguish between actual anomalies and thickness variations.

It has been proposed to compensate for thickness or part geometry variations during ultrasonic inspection by detecting signal reflections from within the part, preferably reflections from a surface of the part opposite an ultrasound transponder. This technique is sometimes referred to as bottom echo detection. By measuring the time between transmission and reception of an ultrasound signal, and knowing the attenuation characteristics of the part being inspected, one can compute the part thickness. This technique, however, is fraught with disadvantages since internal reflections are also generated from anomalies in the part. Furthermore, relatively thick parts may require high energy ultrasound since the sound must travel through twice the thickness of the part.

With parts of varying thickness, another problem that occurs is that a change in thickness creates a change in the amplitude of a received ultrasonic signal, which change may appear as an anomaly, but which also may create a received signal amplitude which falls outside the dynamic range of the receiver. If, for example, the part varies from a thick to a thin geometry, the received signal may be so large as to saturate the receiver thus precluding obtaining of useful data.

SUMMARY OF THE INVENTION

Among the several objects of the present invention may be noted the provision of a method for continuous measurement of thickness of a part being inspected; the provision of a method for compensating for thickness variations in a part being inspected; the provision of a method for compensating for signal strength outside the dynamic range of a single receiver; and the provision of a method for developing a C-scan image of a part of varying thickness.

The above and other objects, features, and advantages are obtained in a method which locates and identifies defects in a variable geometry workpiece using first and second transceivers positioned adjacent opposite surfaces of the workpiece and aligned to direct ultrasonic signals toward each other through the workpiece. The method comprises transmitting a signal at a predetermined frequency toward the opposed workpiece surfaces from respective ones of the transceivers. Reflections of the signal are detected from each of the workpiece surfaces at a respective one of the transceivers. The distance from each of the transceivers to the corresponding workpiece surface is computed from the time delay between the transmitting step and the detecting step. To obtain the thickness of the workpiece, the distance from each of the transceivers to the corresponding workpiece surface is subtracted from the distance between the transceivers. At one of the transceivers, a signal is detected from another transceiver passing through the workpiece, thereby determining the intensity of the signal passing through the workpiece. The signal intensity is normalized in proportion to the obtained workpiece thickness to establish a signal intensity independent of workpiece thickness in accordance with the relationship: $A_o = A_d * e^{l*d}$, where l is the attenuation coefficient, d is the thickness of the workpiece at a measurement point, and $A_d$ is the detected signal intensity.

The method of the present invention comprises a transceiver which includes at least three signal processing paths with each of the paths having a different preselected gain for providing three signals of different amplified intensities. Furthermore, the method includes establishing a maximum processable signal intensity, and selecting from each of the three amplified intensity signals the signal having the greatest amplitude not exceeding the established maximum processable signal. The actual intensity of the signal passing through the workpiece is computed by correlating the amplitude of the selected one of the three signals with the gain of the channel from which the signal is selected. The logarithm of the actual intensity is calculated from the signal obtained from the step of selecting. Thereafter, the calculated logarithm is displayed on an intensity responsive display, and the step of establishing through the step of displaying for each point on the workpiece through which a signal is transmitted is repeated for developing an ultrasound image of the workpiece.

BRIEF DESCRIPTION OF THE DRAWINGS

For a better understanding of the present invention, reference may be had to the following detailed description taken in conjunction with the accompanying drawings in which.

DETAILED DESCRIPTION OF THE INVENTION

Figure 1:
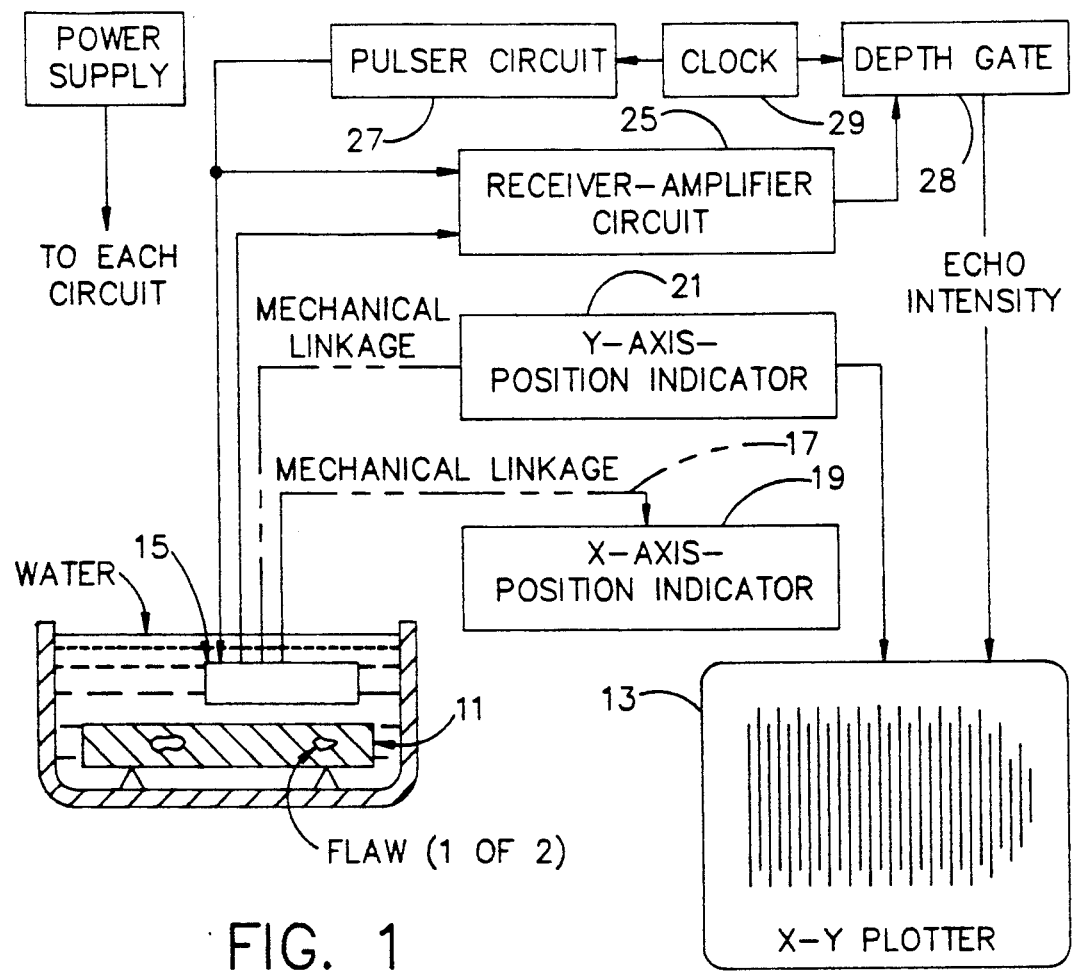
FIG. 1 is a simplified block/schematic diagram of an exemplary C-scan ultrasound inspection system.

Basic ultrasonic inspections systems are well known and the various elements of such systems are commercially available. Exemplary systems for A-scan, B-scan, and C-scan are shown in the *Metals Handbook*, 8th edition, vol. 11, published by American Society for Metals, Metals Park, Ohio. A typical system for obtaining a C-scan is shown in FIG. 1. In this illustrative system, an image is obtained by recording echoes from internal portions of the object 11 as a function of the position of each reflecting interface within an area. Flaws or anomalies are shown on a display 13 in a plan view with both flaw size and location being displayed. Data is obtained by scanning or moving a transponder 15 over the surface of the object 11 in a search pattern. Mechanical linkage 17 connects the transponder to x-axis and y-axis position indicators 19, 21 which provide position data to the display 13. The display may indicate flaws by variation in shading (gray scale) or by an absence of shading as shown in the figure. The electronic depth gate 28 is necessary to allow only those signals received within a limited range of delay times following the transmitted pulse to be admitted to receiver amplifier circuit 25. The depth gate may be set, for example, so that reflections from the front surface and the back surface are excluded so that only reflections from internal anomalies are displayed. The pulser circuit 27 provides the ultrasound pulse while the clock 29 produces timing signals for the system.

The system of FIG. 1 presumes uniform thickness of the object 11. If this thickness is not uniform, the information at display 13 will not be accurate. One attempt to compensate for thickness variation involves positioning the transponder 15 in contact with the object 11 such that the front surface of the object coincides with the transponder surface. Thickness can then be obtained by detecting the reflected signal from the bottom surface of the object. It will be appreciated that such a technique is prone to error due to multiple reflections within the object and to reflections from anomalies adjacent the bottom surface.

Figure 2:
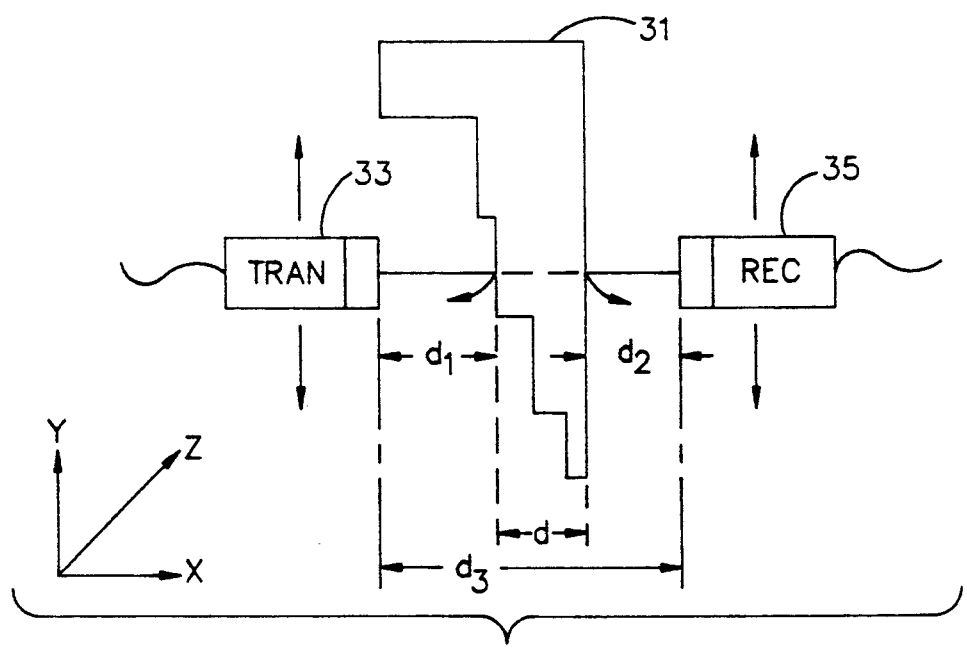
FIG. 2 is a simplified block diagram of an irregular object being inspected by oppositely placed ultrasound transponders.

The present invention is indicated schematically in FIG. 2. An object 31 having a non-uniform thickness is positioned between a pair of transponders 33, 35. The object is scanned in the y-z plane while maintaining a fixed spacing between the transponders. In a pulse-echo mode of operation, each transponder 33, 35 transmits an ultrasound signal and listens for the first reflection of the signal. By timing the receipt of the first reflected signal or echo with respect to the time of transmission, and knowing the velocity of the ultrasound signal in water, the distance from the transponder to the object surface can be computed, i.e., $d = vt$ where d is the distance from transponder to object, v is the velocity of the ultrasound signal in water and t is the time between transmission and reception. If $d_1$ is the distance between transponder 33 and an adjacent surface of object 31, $d_2$ is the distance between transponder 35 and an adjacent surface of object 31, and $d_3$ is the distance between transponders 33 and 35, then the thickness d of the object at any point is given by $d = d_3 - d_1 - d_2$. This method of determining thickness avoids the disadvantages discussed above with respect to prior systems.

Once the object thickness d has been determined, the system of FIG. 2 can operate in a through transmission mode in which one transponder acts as a transmitter while the other acts as a receiver. In order to display a plan view of the object 31, the through transmission data must be corrected for object thickness. Such correction can be made by computing for each point in the object a compensated received signal. If $A_d$ is the amplitude of a through transmission signal at a thickness of d from the front surface, i.e., the surface from which the signal is transmitted, and l is the attenuation coefficient of the material of which the object is formed, the amplitude $A_o$ of the signal without the thickness effect is given by:

$$A_o = A_d * e^{l*d}$$

A plot or display of the values of $A_o$ against x-y coordinates provides an image of the object without attenuation variation due to thickness while retaining any information due to internal anomalies in the object.

While FIG. 2 only indicates a pair of transponders, it will be appreciated that the system includes many of the elements of FIG. 1, including an electronic depth gate, a clock, a pulsar circuit, a receiver-amplifier circuit, y-axis and z-axis position indicators and a display or recorder. Preferably, the system is implemented in the form indicated in FIG. 3. The ultrasonic signals are generated and received by a pulsar/receiver such as a Krautkramer Branson Corp, Model KB6000 which includes a CRT display, a receiver, an ultrasonic pulsar and an electronic depth gate. The scanner is a Caldata Corp. eleven axis, eight channel dual bridge scanner. The display is preferably a color CRT monitor coupled to a color printer for providing color images of an object in which color indicates levels of attenuation. The system is timed and controlled by a Digital Equipment Corp. computer such as the PDP 11/73.

Figure 3:
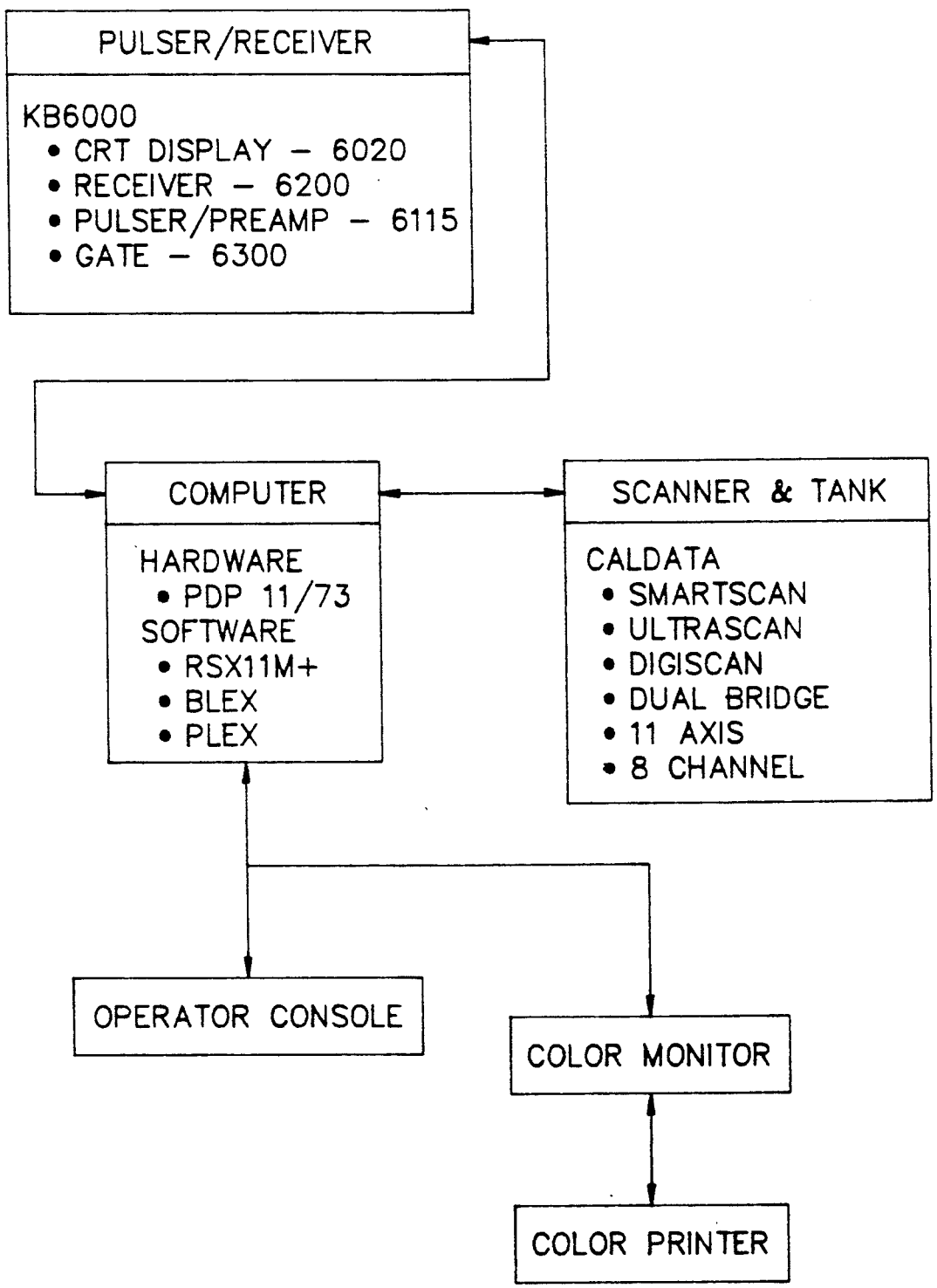
FIG. 3 is a block diagram of a system according to one form of the present invention.
Figure 4A:
FIGS. 4A-4D are C-scan representations of an object inspected with the system of FIG. 3.

As previously discussed, there are often problems with receiver saturation due to lack of dynamic range when imaging objects of widely varying thickness. In the system of FIG. 3, this problem is overcome by using at least three different receiver amplifiers each having a different gain setting. Referring to FIGS. 4A-4D, there is shown in FIG. 4A an image obtained at a first relatively low receiver gain. The black areas indicate lack of penetration of the ultrasonic signals due to high attenuation caused either by thickness or defects in the object. White areas indicate low attenuation and good penetration of the ultrasonic signals. It can be seen that a large portion of this image conveys little information about the object.

Figure 4B:
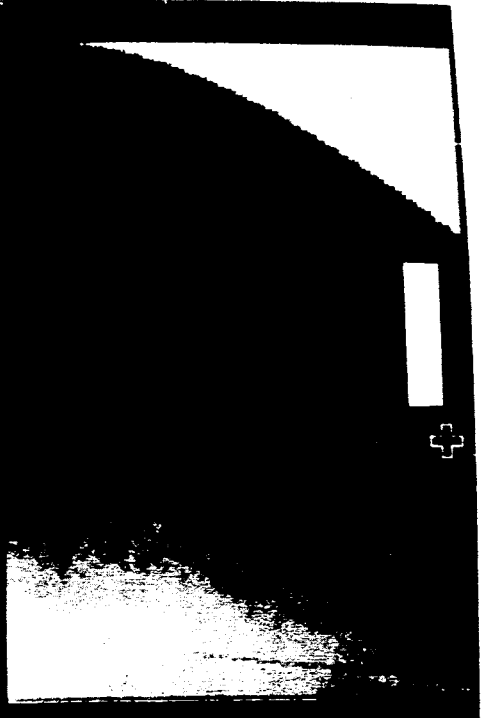
Figure 4C:
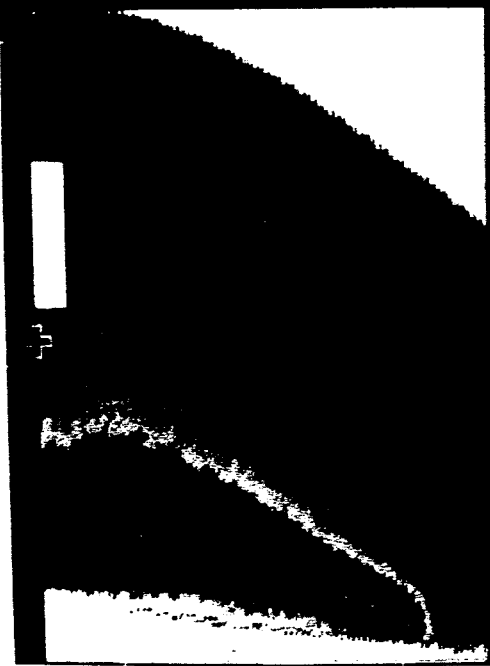

FIG. 4B shows the same object as imaged from a receiver channel at a higher gain than in FIG. 4A. Here, the area without penetration has been significantly reduced. However, anomalies or flaws in the high penetration area have been washed out by the higher signal amplitude through this receiver channel. In FIG. 4C, there is shown the same object imaged at a still higher gain to further reduce the unpenetrated areas to only the very thick portions of the object.

Figure 4D:
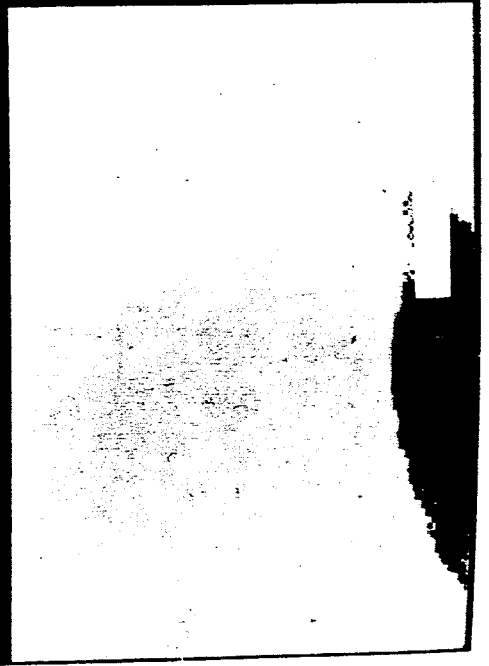

Using the signals from which the images in FIGS. 4A, 4B, and 4C were constructed, the present invention creates the image shown in FIG. 4D which shows the object with only the meaningful data extracted from each channel. The image in FIG. 4D is actually derived from the logarithm of the data obtained from the highest unsaturated signal from the three channels. Considering a system employing a digital-to-analog converter (A/D) with a limited range such that each data point is limited to 7 bits, the maximum signal becomes 127. Any data valve that exceeds this maximum is considered saturated and is set to 127 by the A/D converter. If the gain values of channels 1, 2, and 3 are set to 10 db, 30 db, and 50 db, respectively, channels 2 and 3 will have an amplification factor of 10 and 100, respectively, with regard to channel 1.

TABLE 1

| Actual Data | | | Acquired Data | | | Selected Values-Chan | | Stored Data |
|---|---|---|---|---|---|---|---|---|
| Ch1 (1×) | Ch2 (10×) | Ch3 (100×) | Ch1 | Ch2 | Ch3 | | | |
| 1 | 2 | 3 | 4 | 5 | 6 | 7 | 8 | 9 |
| 1 | 10 | 100 | 1 | 10 | 100 | 100 | 3 | 100 |
| 2 | 20 | 200 | 2 | 20 | 127 | 20 | 2 | 200 |
| 12 | 120 | 1200 | 12 | 120 | 127 | 120 | 2 | 1200 |
| 15 | 150 | 1500 | 15 | 127 | 127 | 15 | 1 | 1500 |
| 100 | 1000 | 10000 | 100 | 127 | 127 | 100 | 1 | 10000 |
| 127 | 1270 | 12700 | 127 | 127 | 127 | 127 | 1 | 12700 |

Table 1 illustrates a 3-channel system with the above defined gains. The actual data signal values are listed in the left hand columns 1-3 after processing through the respective receiver-amplifier in each channel. The acquired data is the values set by the system with 127 being the maximum allowed value and is shown in columns 4-6. Note that the data in channel 2 is saturated or exceeds the maximum processable signal of 127 for all signals greater than 12 in channel 1, as shown in Table 1, while the data in channel 3 is saturated for all signals greater than 1 in channel 1, as shown in Table 1. The right-hand columns 7-8 indicate the data selected and the channel from which it was selected. Using these data values and the gain of the channel from which the data was obtained, the actual value of the data can be reconstructed as shown in column 9. The range of data values in column 9 can vary from 0 to 12700. In order to increase display accuracy for both small and large values, the logarithms of the values in column 9 are used to create the image in FIG. 4D.

Figure 5:
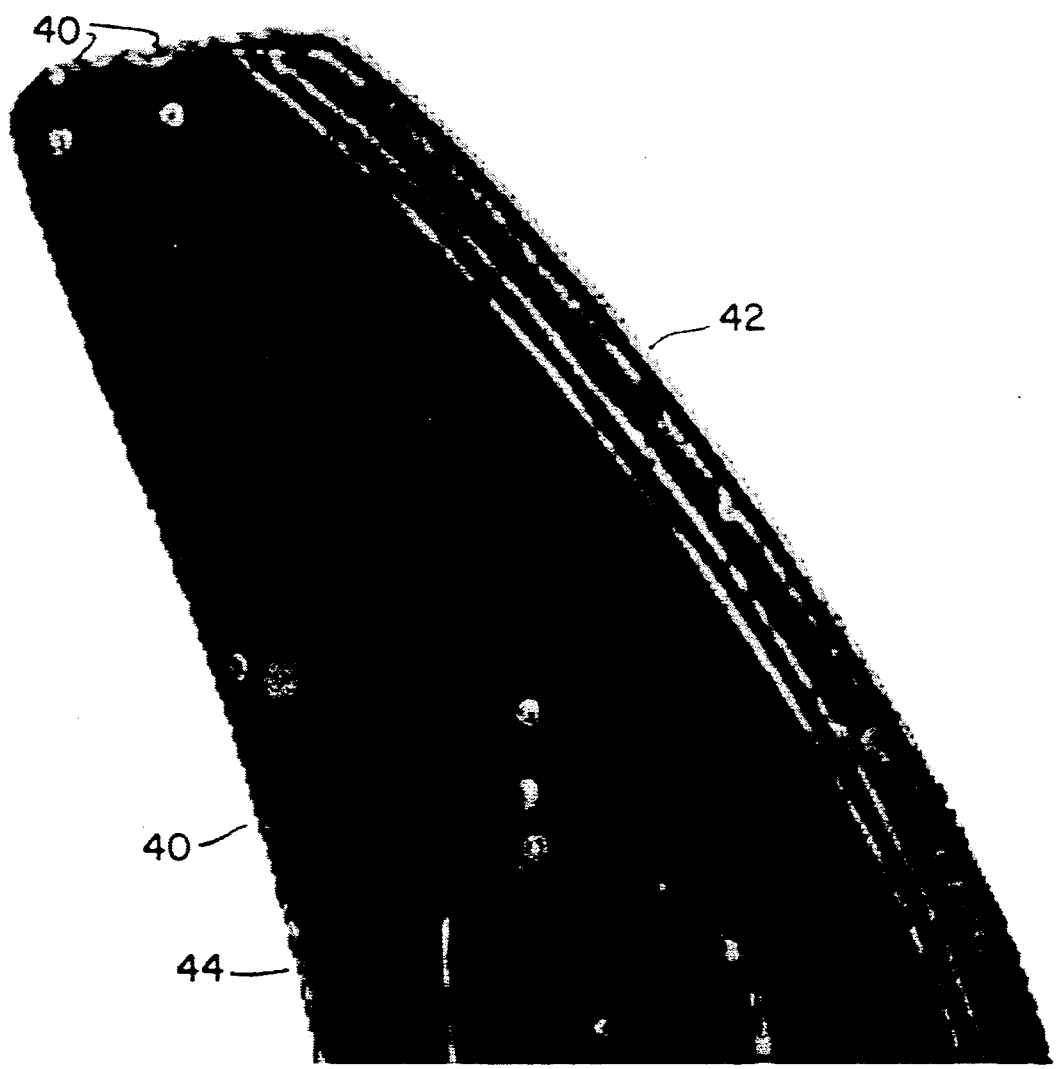
FIG. 5 is a composite image obtained from the system of FIG. 3.

FIG. 4D shows variations in through transmission amplitude due to thickness changes and possible anomalies or flaws in the object being inspected. It is desirable to remove this thickness effect in order to provide an image which only indicates anomalies in the object. FIG. 5 is an image of the object shown in FIG. 4D with the thickness effect removed. As described above, the thickness effect is deleted by adjusting each of the data values, in accordance with the expression $A_o = A_d * e^{l*d}$ and thereafter displaying the computed values of $A_o$. The image in FIG. 5 not only shows flaws as darker spots, indicated at 40, but also shows the outline of the object being inspected which, in this case, is an aircraft propeller blade of a composite material. The dark leading edge at 42 is a metal protector while the dark area at 44 is an internal support spar.

The method described above which is implemented in the system of FIG. 3 with the PDP-11/73 performing the logarithmic and thickness compensation calculations, provides an easy way to interpret C-scan display by eliminating signal variations due to thickness. The use of multiple channels with different gain settings provides a higher dynamic range for data acquisition so that both small and large anomalies can be imaged in the same display. Quantitative data is available for each detected anomaly.

While the invention has been described in what is presently considered to be a preferred embodiment, many variations and modifications will become apparent to those skilled in the art. It is intended therefore that the invention not be limited to this embodiment but be interpreted within the spirit and scope of the appended claims.

What is claimed is:

1. A method for locating and identifying defects in a variable geometry workpiece using first and second transceivers positioned a preselected distance apart adjacent opposite surfaces of the workpiece and aligned to direct ultrasonic signals toward each other through the workpiece, the method comprising the steps of:
    transmitting a signal at a predetermined frequency toward the opposed workpiece surfaces from respective ones of the transceivers;
    detecting reflections of the signal from each adjacent one of the workpiece surfaces at a respective one of the transceivers;
    computing, from the time delay between the step of transmitting and the step of detecting, the distance from each of the transceivers to the corresponding workpiece surface;
    subtracting the distance from each of the transceivers to the corresponding workpiece surface from the distance between the transceivers to obtain the thickness of the workpiece;
    detecting at at least one of the transceivers a signal from the other of the transceivers passing through the workpiece;
    determining the intensity of the signal passing through the workpiece; and
    normalizing the signal intensity in proportion to the obtained workpiece thickness to establish a signal intensity independent of workpiece thickness in accordance with the relationship: $A_o = A_d * e^{l*d}$, where l is the attenuation coefficient, d is the thickness of the workpiece at a measurement point, $A_d$ is the detected signal intensity, and $A_o$ is the normalized signal intensity.

2. The method of claim 1 wherein the at least one of the transceivers includes at least three signal processing paths, each of the paths having a different preselected gain for providing three signals of different amplified intensities, the method including the further steps of:
    establishing a maximum processable signal intensity;
    selecting from each of the three amplified intensity signals the signal having the greatest amplitude not exceeding the established maximum processable signal;
    computing from the selected one of the three signals the actual intensity of the signal passing through the workpiece by correlating the amplitude of the selected one of the three signals with the gain of the channel from which the signal is selected;
    calculating the logarithm of the actual intensity of the signal obtained from the step of selecting;
    displaying the calculated logarithm on an intensity responsive display; and
    repeating the steps of establishing through the step of displaying for each point on the workpiece through which a signal is transmitted for developing an ultrasound image of the workpiece.

3. A method for locating and identifying defects in a variable geometry workpiece, comprising the steps of:
    (a) positioning first and second transceivers adjacent opposite surfaces of the workpiece;
    (b) aligning the transceivers to direct ultrasonic signals toward each other through the workpiece, at least one of the transceivers including at least three signal processing channels, each of the channels having a different preselected gain for providing three signals of different amplified intensities
    (c) establishing a maximum processible signal intensity;

(d) selecting from each of the three amplified intensity signals a signal having the greatest amplitude not exceeding the established maximum processable intensity;

(e) computing from the selected one of the three signals an actual intensity of the signal passing through the workpiece by correlating the amplitude of the selected one of the three signals with the gain of the channel from which the signal is selected;

(f) displaying a signal intensity corresponding to the actual intensity on an intensity responsive display;

(g) repeating the steps (c)-(f) for each point on the workpiece through which a signal is transmitted for developing an ultrasound image through the workpiece; and (h) locating and identifying any defects in the workpiece by observing any dark spots on the ultrasound image.

4. The method of claim 3, wherein the displayed signal intensity in step (f) is obtained by calculating the logarithm of the actual intensity of the signal computed in step (e).

5. The method of claim 3 and including the further step of compensating each of the displayed signal intensities to remove attenuation effects caused by variations in part thickness.

6. The method of claim 5 wherein the step of compensating includes the step of computing a compensated thickness signal in accordance with the relationship $A_o = A_d * e^{l*d}$, where l is the attenuation coefficient of the workpiece material, d is the thickness of the workpiece at each signal intensity measurement point, $A_d$ is the detected signal intensity and $A_o$ is the compensated signal intensity.

* * * * *